United States Patent [19]

Kleinberg

[11] Patent Number: 5,155,509
[45] Date of Patent: Oct. 13, 1992

[54] OBLIQUE ILLUMINATION DEVICE FOR USE WITH AN OPHTHALMIC MICROSCOPE

[75] Inventor: Larry K. Kleinberg, Toluca Lake, Calif.

[73] Assignee: Storz Instrument Company, St. Louis, Mo.

[21] Appl. No.: 603,464

[22] Filed: Oct. 25, 1990

[51] Int. Cl.⁵ ............................................. A61B 3/10
[52] U.S. Cl. .................................... 351/205; 351/214; 351/221
[58] Field of Search ............... 351/205, 206, 214, 216, 351/221

[56] References Cited

U.S. PATENT DOCUMENTS

| | | | |
|---|---|---|---|
| 3,944,343 | 3/1976 | Mueller, Jr. | 351/221 |
| 4,932,774 | 6/1990 | Takagi et al. | 351/214 |

OTHER PUBLICATIONS

Survey of Ophthalmology, Jan.-Feb., 1990, article by Michels and Sternberg, "Operating Microscope-Induced Retinal Photoxicity; Pathophysiology, Clinical Manifestations and Prevention".

*Primary Examiner*—Paul M. Dzierzynski
*Attorney, Agent, or Firm*—Brooks & Kushman

[57] ABSTRACT

Oblique illumination system is provided for use with an ophthalmic microscope having a direct illumination system. The apparatus includes a first light deflector for deflecting light in the direct illumination axis transversely along a transverse axis. A first support movably connects the first light deflector to enable it to be shifted into and out of the direct illumination axis; a second light deflector redirects the light in the transverse axis along an oblique axis which intersects the microscope axis at the focal plane. The first light deflector can be alternatively shifted to vary the microscope between the direct and indirect illumination modes to minimize the duration of the exposure of the eye macula to the illumination system during a surgical procedure. A method for converting a conventional direct illumination operating microscope for use as an indirect illumination microscope is also provided.

16 Claims, 3 Drawing Sheets

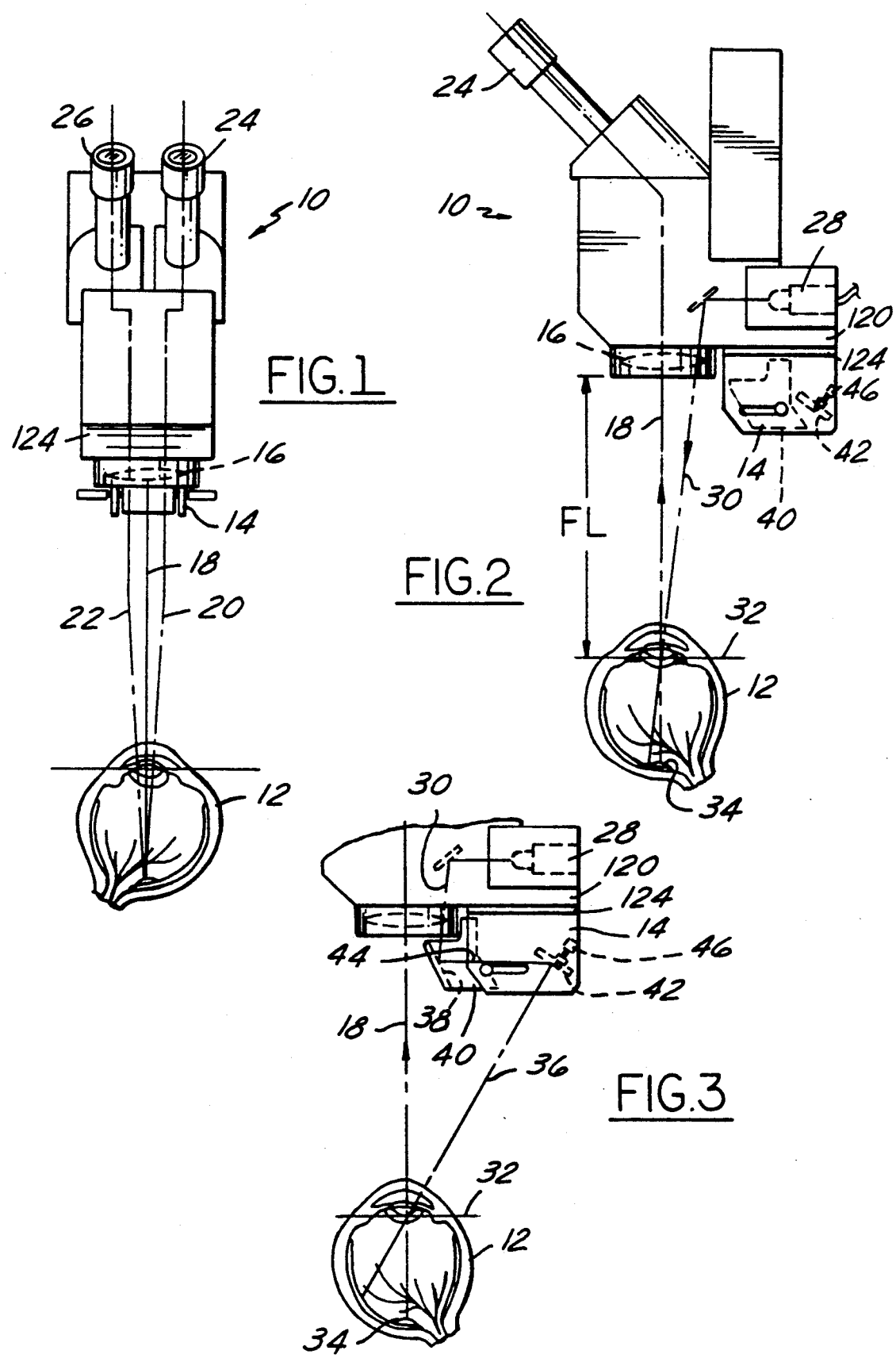

OBLIQUE ILLUMINATION DEVICE FOR USE WITH AN OPHTHALMIC MICROSCOPE

TECHNICAL FIELD

This invention relates to microscope illumination systems and more particularly to illumination systems capable to alternatively providing direct or indirect illumination to a patient's eye during a surgical procedure.

BACKGROUND ART

It has long been recognized that retinal damage can result from the exposure of the retina to an intense light. The amount of damage is dependent upon the intensity of the light and the duration or period of time that the retina is exposed to the light. Recently, the medical community has begun to recognize instances of light induced retinal damage resulting from exposure to the intense light of an operating microscope illumination system. This problem is described in detail in an article by Michels and Sternberg, "Operating Microscope-Induced Retinal Phototoxicity; Pathophysiology, Clinical Manifestations and Prevention" published in the Survey of Ophthamology, Jan.-Feb., 1990, pages 237 to 252, which is incorporated by reference herein.

It is pointed out in the Michels and Sternberg article that the onset and severity of light-induced retinal damage is affected by the intensity of the light per unit area of retina exposed (watts per centimeter squared), the duration of exposure (minutes) and the wave length of the light source (Nanometers). Additionally, the fovea and the macula portion of the retina appear to be the most sensitive to retinal damage. This is a result of increased photo sensitivity of these acutely sensitive portions of the retina, the fact that damage to this area is much more readily noticed by the patient since the loss will occur in the prime viewing area, or some combination of these two factors.

During eye surgery, particularly during cataract surgery or interocular lens implantation, it is frequently necessary to directly illuminate the eye with an illumination source generally coaxially aligned with the microscope axis. The direct illumination axes are typically inclined relative to one another 3° to 6° and generally intersect one another at the focal plane of the microscope. Light from the microscope illumination system will pass through the eye and will be directed upon the macula portion of the patient's retina.

During a significant portion of any eye surgery procedure, it is also frequently not necessary to directly illuminate the eye. It is during these times that indirect illumination from an oblique light source can be utilized so as to minimize the duration of exposure of the macula to the microscope illumination system.

In order to minimize the likelihood of light induced retinal damage from an operating microscope illumination system, one manufacturer has proposed a counter which would monitor the cumulative exposure of the patient's retina to light. This is a product of a light intensity and the duration of exposure. Utilizing this monitoring technique, the ophthalmologist could appropriately limit the duration of the procedure in order to not overexpose the patient's retina to light. Others have proposed filtering out ultra violet and infrared portions of the illumination light spectrum in order to minimize the total energy absorbed by the retina of the patient's eye. Finally, by microscopes having dual illumination systems, a direct generally coaxial illumination system as well as a secondary illumination system having light directed upon the eye at an oblique angle relative to the microscope is being utilized. Microscopes having dual illumination systems are necessarily more complex and expensive. Zeiss and Topcon are two microscope manufacturers currently working on dual illumination system microscopes which utilize a pair of secondary light sources providing oblique illumination path inclined approximately 20° from the microscope axis. The indirect illumination systems have their own separate light sources. During the surgical procedure when direct illumination is not necessary, the secondary illumination system is activated and the direct illumination system turned off.

DISCLOSURE OF INVENTION

An object of the present invention is to provide a simple effective oblique illumination system for an ophthalmology microscope in order to minimize light induced retinal damage.

Another object of the present invention is to provide an oblique illumination system which can be retrofitted to existing conventional ophthalmology microscopes without necessitating the use of a second illumination source.

Another object of the present invention is to provide an oblique illumination system capable of being adjusted for use at different microscope focal lengths.

Accordingly, the oblique illumination apparatus of the present invention is intended to be used with an ophthalmology microscope having a direct illumination system providing light to the eye of the patient along a direct axis which is closely spaced from the microscope axis adjacent the microscope and intersecting the microscope axis at the focal plane. The oblique illumination apparatus includes a first light deflector for deflecting the light in the direct illumination axis transversely along a transverse axis. The first light deflector is connected to the microscope by a first support enabling the first light deflector to be moved between a direct illumination position, wherein the direct axis is unobstructed, and an indirect illumination position, where the light in the direct axis is redirected transversely. A second light deflector is provided for redirecting the light in the transverse axis along an oblique axis which generally intersects the microscope axis and the microscope focal plane.

Additionally, the method of retrofitting a conventional microscope for alternative direct and indirect illumination is provided where the first light deflector is shifted between the direct and indirect positions during the surgical procedure in order to limit the duration of exposure of certain portions of the patient's retina to the illumination source.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIG. 1 is a front view of a typical binocular microscope shown relative to a schematic illustration of an eye;

FIG. 2 is a side elevation of the binocular microscope of FIG. 1 in the direct illumination mode;

FIG. 3 is a partial side elevational view of the microscope of FIG. 2 showing the oblique illumination apparatus in operation;

BEST MODES FOR CARRYING OUT THE INVENTION

Figure 4:
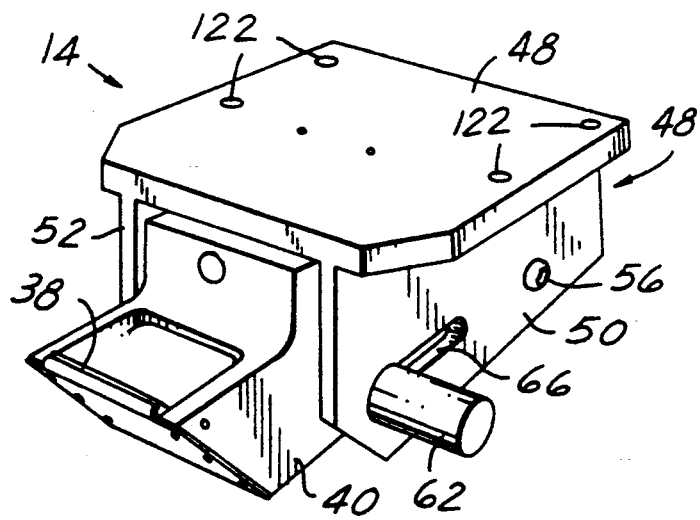
FIG. 4 is an upper perspective view of the oblique illumination apparatus.
Figure 5:
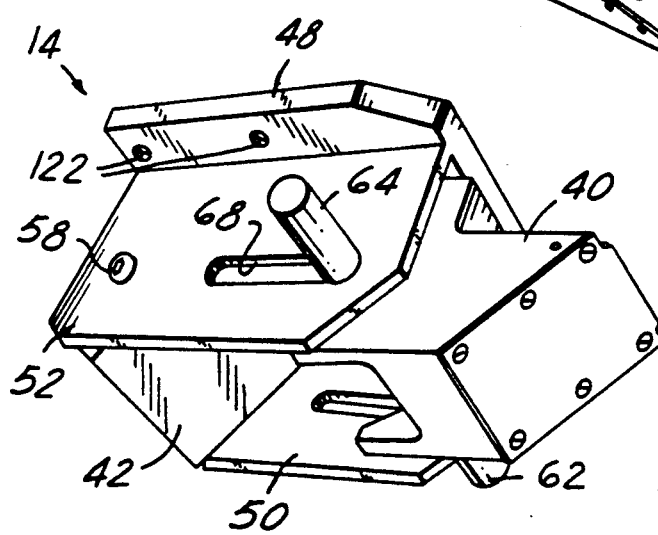
FIG. 5 is a lower perspective view of the oblique illumination apparatus.

With reference to FIGS. 1–7, the first embodiment of the invention will be described.

FIG. 1 illustrates a binocular microscope 10 positioned above the eye 12 of a patient. Oblique illumination apparatus 14 is affixed to the underside of the microscope directly adjacent the microscope objective lens 16. The microscope in the position shown has a generally vertical microscope axis 18 shown bisecting the right and left optic axes 20, 22 which are optically coupled to right and left eye pieces 24 and 26, respectively, in a conventional manner.

The illumination system of the microscope 10 is shown in the direct illumination mode in FIG. 2. Oblique illumination apparatus 14 is inoperative when the microscope is in a direct illumination mode and light passes in a normal fashion from light source 28 (shown schematically) through objective lens 16 and along direct illumination axis 30 to the patient's eye 12. The direct illumination axis intersects the microscope axis at approximately the focal point of the microscope which is located one focal length (FL) from the microscope objective lens. Focal plane designated by line 32 is oriented within the region of the eye at which the opthamologist wishes to observe. The light passing along the direct illumination axis 30 continued on beyond the focal plane passing through the vitreous humor within the posterior cavity of the eye to illuminate a portion of the retina.

When the microscope is set up to look directly into the eye, the direct illumination axis will typically illuminate the macula portion 34 of the retina. When direct illumination of the patient's eye is not necessary, such as during the wound opening and closing portion of the surgical procedure, the oblique illumination apparatus 14 is utilized to create an oblique illumination axis 36 which generally intersects the microscope axis 18 at focal plane 32, but is inclined sufficiently relative thereto so that macula portion 34 is not illuminated. By illuminating a portion of the retina which is spaced significantly from the macula, not only is macula exposure time limited, but in the event there is sufficient light intensity and duration to cause limited light induced retinal damage, the vision impairment will be significantly outside of the patient's primary field of view so as to not unduly hinder the patient's sight.

The oblique illumination axis 14 is made up of three principal components, a first mirror 38, a first mirror support 40, and a second mirror 42. First mirror 38 provides a first light deflecting means for deflecting the light in direct illumination axis 30 transversely along a transverse axis 44. Second mirror 42 reflects the light in transverse axis along indirect illumination axis 36 as illustrated in FIG. 3. First mirror support 40 serves to movably connect the first mirror to the operating microscope so as to enable the first mirror to be alternatively moved between a direct illumination position shown in FIG. 2 where the direct axis 30 is unobstructed, and the indirect illumination position shown in FIG. 3 where the light and the direct axis 30 is redirected transversely along transverse axis 44. The preferred first mirror support 44 consists of a simple slide mechanism which enables the mirror to be alternatively moved generally radially to the microscope axis.

The illumination apparatus 14 can be attached to the microscope in any permanent or removable manner. The apparatus 14 can be screwed or otherwise fixedly secured to the microscope housing 120 by means of fasteners (not shown) being inserted through holes 122 in frame member 48. Alternately, the apparatus 14 can be removably or releasably attached to the microscope housing by any conventional mechanism, such as groove and slide means, set screws, clips and the like.

It should be appreciated that direct illumination axis 30 is not truly coaxial with microscope axis 18 even though this mode of illumination is frequently referred to as "coaxial illumination." Direct axis 30 is adjacent to and spaced from the microscope axis at the microscope objective lens and only intersects the microscope axis at the focal plane. (Although axis 30 in practice is typically spaced only a few degrees from axis 18, it is shown further apart in the drawings simply for illustrative purposes). It is, therefore, possible to obstruct the direct illumination access without hindering the right and left optic axes 20, 22 of the binocular microscope viewing system.

To accommodate microscopes having various focal lengths, second mirror 42 is pivotably attached to the microscope so that the inclination of the indirect axis can be varied in order to cause the indirect axis to intersect the microscope axis at the appropriate focal length. In order to facilitate adjustment of the second mirror, second mirror handle 46 is used to rotate the mirror about a generally horizontal axis.

The detailed structure of the oblique illumination apparatus 14 is illustrated in FIGS. 4–7. To facilitate the simple installation of the oblique illumination apparatus to existing conventional microscopes, frame member 48 is provided having a flat surface for attachment to the microscope housing 120 in a system generally adjacent to the objective lens. (The apparatus 14 could also be attached to the illumination housing or module). Frame member 48 has a pair of downwardly depending side wall members 50 and 52 to which is mounted first mirror support 40 and second mirror 42. Second mirror 42 is mounted on a mirror retainer 54 pivotably connected to side walls 50 and 52 by screws 56 and 58 which enable the mirror to be rotated about a generally horizontal axis utilizing second mirror handle 46 which extends outwardly from mirror retainer 54. First mirror support 40 is mounted upon on frame support 48 utilizing a guide rod mechanism 60. The guide rod 60 is an elongated cylindrical rod slidingly mounted in support 61 which is attached to a recessed area 63 in the frame portion 48. One end of the guide rod 60 is affixed to first mirror support 40 and the other end slidably cooperates with a cylindrical opening 65 in the support 61. In the preferred embodiment illustrated, a spring and ball detent/tensioner 67 is provided to securely retain the first mirror support in position relative to the microscope.

Figure 6:
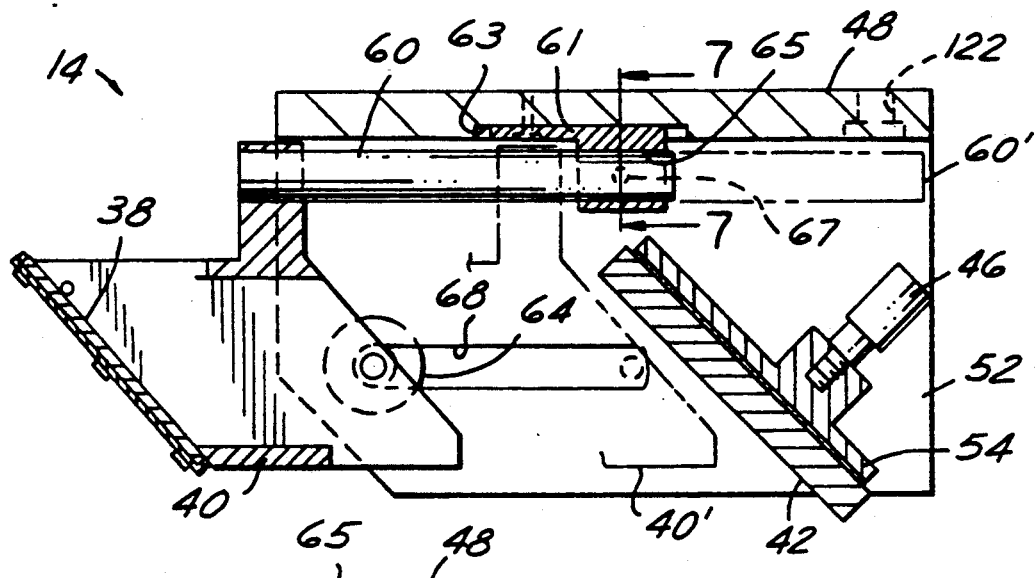
FIG. 6 is a cross-sectional side elevational view of the oblique illumination apparatus.
Figure 7:
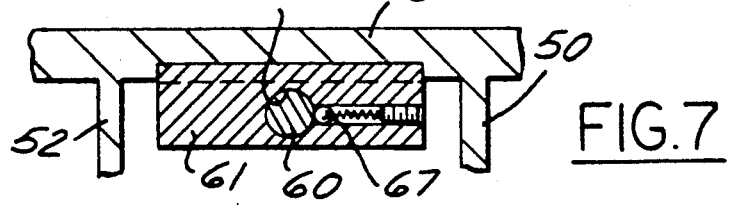
FIG. 7 is a cross-sectional view take along line 7—7 of FIG. 6.

In order to facilitate the sliding movement of the first mirror between the direct and indirect positions, a pair of handles 62 and 64 are provided which extend outwardly from mirror support 40 through slots 66 and 68 in wall members 50 and 52, respectively. The handles and slots serve to further limit the relative movement of the first mirror support. FIG. 6 illustrates the range of movement of the first mirror support 40 from its stored position 40' allowing direct illumination to its extended position facilitating oblique illumination.

It should be appreciated, of course, that while the preferred embodiment of the invention illustrated utilizes front surface mirrors to provide a means for deflecting light, second surface mirrors or prisms may alternatively be used for the same purpose. Front surface mirrors are preferred, however, due to their ability to reflect light with minimum attenuation. It should be also appreciated that while the mirrors illustrated are flat, a contour mirror could be used particularly if it was desired to further focus the light in the indirect illumination axis to compensate for the additional dispersion resulting from the increase in the light path length. Along the same lines, the first support could be movably attached to the microscope utilizing a different type of functionally equivalent mechanism.

Alternately, an optic element such as a lens or filter (not shown), could also be inserted within the illumination light path in the illumination apparatus 14 in order to focus or alternate the light as desired. For illustrative purposes, such a lens 140 is shown in phantom lines in the alternate oblique illumination apparatus 70 shown in FIG. 8.

Figure 8:
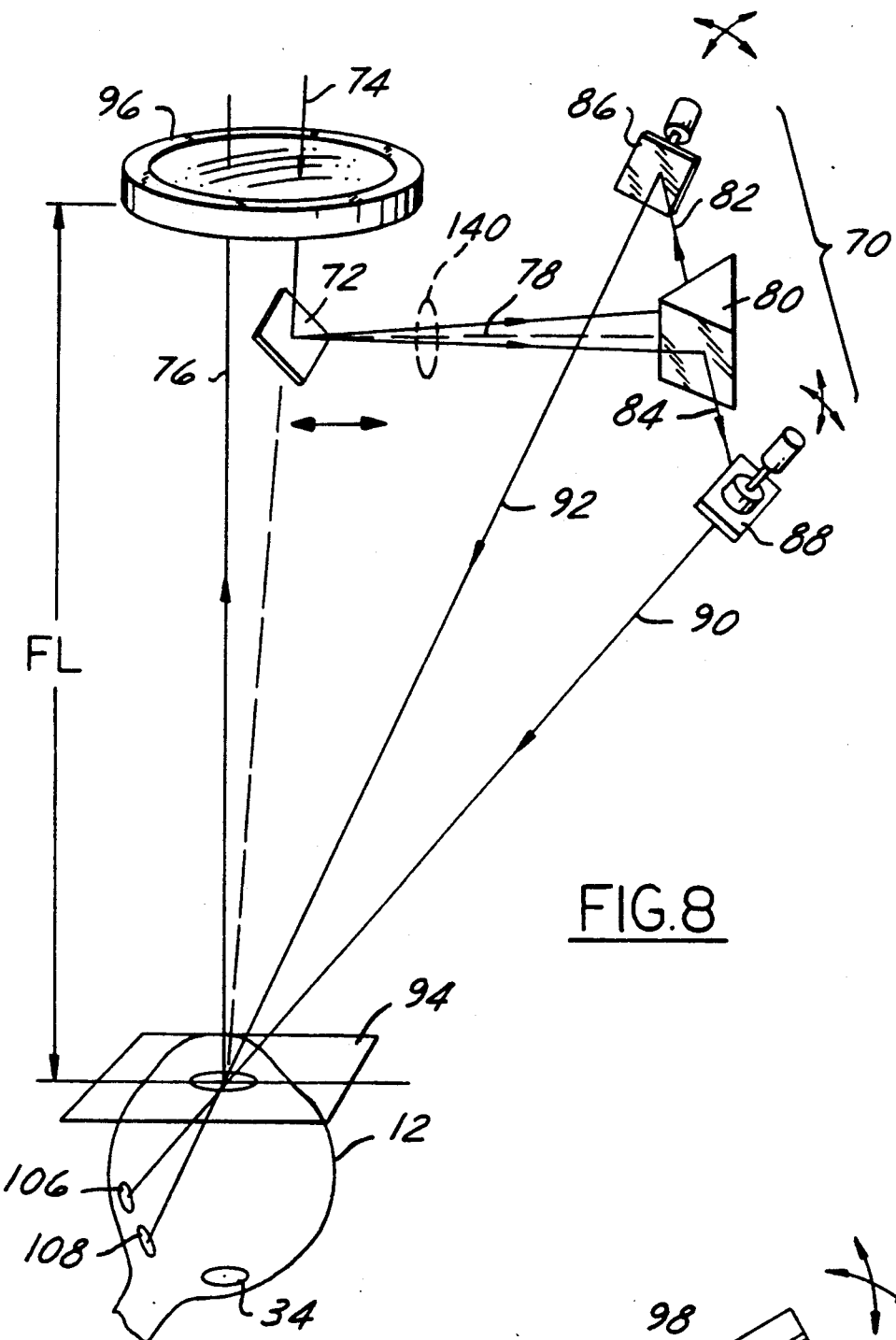
FIG. 8 is a perspective schematic illustration of an alternative embodiment of the invention.

An alternative embodiment of the invention is illustrated schematically in FIG. 8. Oblique illumination apparatus 70 is made up of a first mirror 72 which is movably connected to the microscope utilizing a first mirror support 40 illustrated previously. First mirror 72 located in the indirect illumination position shown in FIG. 8 redirects light from the direct axis 74 transversely along a transverse axis 78 which is generally perpendicular to the microscope axis 76. Light in the transverse axis 78 is bisected by beam splitter 80 which forms a pair of lateral axes 82 and 84 extending outwardly from the beam splitter as illustrated. Lateral mirrors 86 and 88 are aligned with the lateral axis and redirect light therein to form a pair of oblique axes 90 and 92 which generally intersect the microscope axis 76 at focal plane 94. As in the previously described embodiment, focal plane 94 is positioned one focal length from the microscope objective lens 96.

Figure 9:
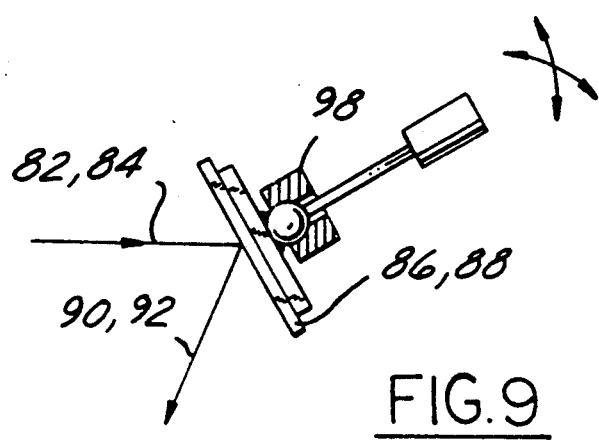
FIG. 9 is an enlarged partial cut-away side elevation of one of the lateral mirrors of the second embodiment of the invention.

In order to accommodate the varying focal lengths, it is necessary to mount the lateral mirrors on a ball and socket type joint 98 illustrated in FIG. 9 so that each of the mirrors can be independently adjusted to properly intersect a microscope axis at the focal point.

By utilizing the oblique illumination apparatus 70 having a pair of spaced apart oblique axes 90, 92, the area of the retina of the eye 12 illuminated can be doubled and correspondingly the power intensity in watts per centimeter squared can be cut in half. Preferably, the oblique axes 90, 92 will be inclined at least 20° from one another and the microscope axis so that the portions 106 and 108 of the retina illuminated by the light travelling along each of the oblique axes will not overlap with one another or the macula portion 34 of the retina.

While not illustrated, it should be appreciated that the beam splitter 80 and the two lateral mirrors 86 and 88 can be fixed to a frame similar to, but slightly wider than, frame 48 illustrated in the first embodiment and first mirror 72 can be movably attached to the microscope in a similar manner as previously described. Beam splitter 80 is a conventional right triangular prism having reflective mirror exterior surface and can be mounted inside the apparatus 70.

While the best mode for carrying out the invention has been described in detail, those familiar with the art to which this invention relates will recognize various alternative designs and embodiments for practicing the invention as defined by the following claims.

What is claimed:

1. An oblique illumination apparatus for use with an ophthalmic microscope having a direct illumination system providing light to the eye of a patient along a direct axis which is closely spaced from the microscope axis adjacent the microscope and intersecting the microscope axis at the focal plane, said apparatus comprising:

first light deflecting means for deflecting the light in the direct axis transversely along a transverse axis;

a first support movably connecting the first light deflecting means to the microscope enabling the first light deflecting means to be alternatively moved between a direct illumination position wherein the direct axis is unobstructed and an indirect illumination position wherein the light in the direct axis is redirected transversely; and a second light deflecting means for redirecting the light in the transverse axis along one or more oblique axes which generally intersect the microscope axis at the focal plane;

said second light deflecting means comprising a beam splitter for bisecting the transverse axis into a pair of lateral axes extending outwardly therefrom, and a pair of lateral mirrors reflecting the light in the lateral axes forming a pair of oblique axes which generally intersect one another in the microscope axis at the focal plane.

2. The invention of claim 1 further comprising a second support pivotably connecting the second light deflecting means to the microscope enabling the distance from the microscope and the intersection of the oblique and microscope axes to be varied to accommodate changes in microscope focal length.

3. The invention of claim 1 wherein the first support further comprises a slide mechanism connecting the first light deflecting means to the microscope allowing the first light deflecting means to be moved transversely through a limited range.

4. The invention of claim 3 wherein the first light deflecting means moves along the transverse axis.

5. The invention of claim 3 further comprising a second support independently connecting the second light deflecting means to the microscope so that the second light deflecting means remains fixed when the first light deflecting means is shifted between the direct and indirect illumination positions.

6. The invention of claim 1 wherein the oblique axis is oriented at a sufficient angle relative to the microscope axis so that the light is not directly focused upon the macula of the patient's eye.

7. The invention of claim 6 wherein the oblique axis is oriented between 20° and 30° relative to the microscope axis.

8. The invention of claim 1 wherein the oblique axes are oriented at a sufficient angle relative to each other and the microscope axis so that the two portions of the retina illuminated by the axes are spaced from each other and the macula thereby reducing the intensity of the light striking the retina and minimizing macula exposure.

9. The invention of claim 8 wherein the oblique axes are oriented 20° from each other and the microscope axis.

10. The invention of claim 1 further comprising a pair of pivotable joints connecting the pair of lateral mirrors to the microscope so that the orientation of the lateral mirrors can be adjusted to maintain the intersection of the oblique axes and the microscope axis in the focal point at various microscope focal lengths.

11. An oblique illumination attachment for use with an ophthalmic microscope having a direct illumination system which provides a light along a direct axis spaced from the microscope axis at the objective lens and intersecting the microscope axis at the focal plane, said attachment comprising:
   an attachment housing having means for removably connecting said housing to the microscope;
   a first mirror in said housing for deflecting the light in the direct axis substantially perpendicular thereto along a transverse axis;
   a first support slidably connecting the first mirror to said housing enabling the first mirror to be alternatively moved between a direct illumination position wherein the direct axis is unobstructed and an indirect illumination position wherein the light in the direct axis is directed transversely by the first mirror;
   said first support being manually slidable between said direct and indirect illumination positions;
   a second mirror in said housing oriented in the transverse axis for redirecting the light therein along an oblique axis which intersects the microscope axis at the focal point; and
   a second support for adjustably connecting the second mirror to said housing enabling the angle of the oblique axis relative to the microscope axis to be varied to accommodate different microscope focal lengths.

12. The invention of claim 11 wherein the oblique axis is oriented at a sufficient angle relative to the microscope axis so that the light is not directly focused upon the macula of the patient's eye.

13. The invention of claim 12 wherein the oblique axis is oriented between 20° and 30° relative to the microscope axis.

14. An oblique illumination apparatus for use with an ophthalmic microscope having a direct illumination system providing light to the eye of a patient along a direct axis which is closely spaced from the microscope axis adjacent the microscope and intersecting the microscope axis at the focal plane, said apparatus comprising:
   an attachment housing having means for removably connecting said housing to the microscope;
   first light deflecting means in said housing for deflecting the light in the direct axis transversely along a transverse axis;
   a first support movably connecting the first light deflecting means to said housing enabling the first light deflecting means to be alternatively moved between a direct illumination wherein the direct axis is unobstructed, and an indirect illumination position wherein the light in the direct axis is redirected transversely;
   said first light deflecting means manually movable between said direct and indirect illumination positions;
   a second light deflecting means in said housing for redirecting the light in the transverse axis along one or more oblique axes which generally intersect the microscope axis at the focal plane; and
   means for attaching said housing to said microscope.

15. The invention of claim 14 further comprising a second support in said housing pivotably connecting the second light deflecting means to said housing enabling the distance from the microscope and the intersection of the oblique and microscope axes to be varied to accommodate changes in microscope focal length.

16. The invention of claim 14 wherein the first support further comprises a slide mechanism connecting the first light deflecting means to said housing allowing the first light deflecting means to be moved transversely through a limited range.

* * * * *